(12) United States Patent
Mori et al.

(10) Patent No.: US 6,313,352 B1
(45) Date of Patent: Nov. 6, 2001

(54) PROCESS FOR PRODUCING CANTHAXANTHIN

(75) Inventors: Toshiki Mori; Naoyuki Katayama; Tsuyoshi Kajiyashiki; Masahiko Kitayama, all of Niigata-ken (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/590,136

(22) Filed: Jun. 9, 2000

(30) Foreign Application Priority Data

Jun. 9, 1999 (JP) .................................................. 11-162577

(51) Int. Cl.$^7$ .................................................. C07C 45/00
(52) U.S. Cl. ........................... 568/348; 568/347; 568/363; 568/364
(58) Field of Search ..................................... 568/348, 347, 568/363, 364

(56) References Cited

U.S. PATENT DOCUMENTS 4,212,827   7/1980   Paust et al. .

*Primary Examiner*—Johann Richter
*Assistant Examiner*—J. Parsa
(74) *Attorney, Agent, or Firm*—Oblon, Spivak, McClelland, Maier & Neustadt, P.C.

(57) ABSTRACT

The present invention provides a process for producing canthaxanthin by mixing β-carotene with an alkali metal chlorate or an alkali metal bromate in water and an organic solvent immiscible with water; adding an iodine halide or iodide; and adding a metal iodide whereby the β-carotene is oxidized to yield canthaxanthin.

14 Claims, No Drawings

PROCESS FOR PRODUCING CANTHAXANTHIN

BACKGROUND OF THE INVENTION

1. Field of the Invention

The present invention provides a process for producing canthaxanthin by mixing β-carotene with an alkali metal chlorate or an alkali metal bromate in water and an organic solvent immiscible with water; adding an iodine halide or iodine; and adding a metal iodide whereby the β-carotene is oxidized to yield canthaxanthin.

2. Related Art of the Invention

Canthaxanthin, a natural colorant, is used as a food dye and as an additive for animal feeds. A process for producing canthaxanthin is disclosed, for example, in U.S. Pat. No. 4,212,827. In this process β-carotene is oxidized with sodium chlorate or sodium bromate in the presence of iodine, bromine, selenium dioxide, vanadium pentaoxide or osmium tetraoxide as a catalyst.

However, in this production process the time necessary for the reaction is from 1 to 250 hours. Furthermore, in order to obtain canthaxanthin with an optimal yield in an advantageous embodiment, at least 20 hours are required (see column 2, lines 33 to 36 of U.S. Pat. No. 4,212,827). Thus, it is recommended that the reaction is conducted for a long time. As an example in which the reaction time is relatively short, Example 12 in the same United States Patent discloses a process for producing canthaxanthin in which 0.00075 mole of sulfuric acid in 20 ml of water is added dropwise continuously over 2 hours at a temperature of 30° C. into a suspension of 10 g of all-trans-β-carotene in 250 ml of chloroform and an aqueous solution containing 20 g of sodium chlorate and 0.4 g of sodium iodide. The reaction is conducted at the same temperature for 3–4 hours. However, if the reaction mixture becomes strongly acidic in the process of the same Example, the resultant product can decompose. Therefore, this process requires that the addition of sulfuric acid is gradually and carefully performed over a long time.

SUMMARY OF THE INVENTION

An object of the present invention is to provide a process for producing canthaxanthin by oxidizing β-carotene with sodium chlorate or sodium bromate for a short time, with efficiency and in an industrially advantageous manner.

The object of the present invention can be achieved by a process described below.

That is, the present invention provides a process for producing canthaxanthin comprising the steps of:
a) mixing β-carotene with an alkali metal chlorate or an alkali metal bromate in water and an organic solvent immiscible with water;
b) adding an iodine halide or iodine; and
c) adding a metal iodide.

DETAILED DESCRIPTION OF THE INVENTION

Examples of iodine halide used in the present invention include iodine chloride, iodine trichloride, iodine bromide, and iodine tribromide. The iodine halide may be used in one or more species. The iodine halide and iodine may be used together.

It is preferred to use iodine in step b).

The amount of the iodine halide or iodine, the total amount of the iodine halide and iodine if the two are used together, is preferably from 1 to 20% and more preferably from 3 to 15% per mole of β-carotene, including 2, 4, 5, 7, 9, 10, 12, 14, 16, 18, 19 and all values and subranges there between.

Examples of a metal iodide used in step c) include lithium iodide, sodium iodide, potassium iodide, magnesium iodide, calcium iodide, silver iodide, copper (I) iodide and copper (II) iodide. It is preferred to use an alkali metal iodide in step c). The metal iodide may be used in one or more species.

The amount of the metal iodide is preferably from 1 to 40% and more preferably from 5 to 30% per mole of β-carotene, including 2, 4, 6, 8, 10, 11, 13, 15, 18, 21, 24, 27, 29, 32, 35, 37, 39 and all values and subranges there between.

In order to produce canthaxanthin efficiently for a short time in the present invention, the molar ratio of the metal iodide to iodine halide or iodine is preferably from 0.5 to 10, and more preferably from 2 to 5, including 1, 1.5, 3, 4, 6, 7, 8, 9.5 and all values and subranges there between.

In the present invention, the combined use of iodine halide or iodine, which can easily dissolve in organic solvents, and the metal iodide, which can easily dissolve in water, makes these components act efficiently as catalysts in water and an organic solvent immiscible with water to give canthaxanthin with a high yield even within a short time.

In the process for producing canthaxanthin according to the present invention, oxidization of β-carotene is started by adding iodine halide or iodine, in step b), and the metal iodide, in step c), to a mixture of β-carotene, water, the organic solvent immiscible with water, and an alkali metal chlorate or an alkali metal bromate.

Iodine halide or iodine, and the metal iodide can be added to the reaction mixture separately or in a form of a mixture thereof. The iodine halide or iodine, and the metal iodide can be added to the reaction mixture continuously or in portion by portion, preferably all at once.

The iodine halide or iodine, and the metal iodide, can be each added to the reaction mixture in a solid form or in the form of solution in a solvent.

The solvent used for dissolving iodine halide or iodine, and the metal iodide, is preferably the same as the mixed solvent comprising water and the organic solvent immiscible with water, used for the oxidization of β-carotene. In this case, the organic solvent is preferably used in an amount of 1:50 to 1:3 of the amount used in the reaction, including 1:48, 1:45, 1:42, 1:39, 1:35, 1:32, 1:28, 1:25, 1:21, 1:17, 1:12, 1:9, 1:7, 1:5 and all values and subranges there between, and the water is preferably used in an amount of 1:50 to 1:30 of the amount used in the reaction, including 1:48, 1:45, 1:42, 1:39, 1:35, 1:32, 1:28, 1:25, 1:21, 1:17, 1:12, 1:9, 1:7, 1:5 and all values and subranges there between.

β-carotene can be commercially available, or prepared by any method described in the literature, e.g., U.S. Pat. No. 4,105,855 and German Patent No. 1068709 incorporated herein by reference.

Examples of the alkali metal chlorate or the alkali metal bromate include lithium chlorate, sodium chlorate, potassium chlorate, lithium bromate, sodium bromate and potassium bromate. The alkali metal chlorate or the alkali metal bromate can be used in one or more species.

The amount of the alkali metal chlorate or the alkali metal bromate is preferably from 1 to 100 times the weight of the β-carotene, including 3, 7, 11, 15, 20, 27, 36, 43, 50, 59, 63, 71, 85, 90, 95 and all values and subranges there between.

In the present invention, water and an organic solvent immiscible with water are used. Examples of the organic solvent immiscible with water include halogenated hydrocarbons such as methylene chloride, chloroform, carbon tetrachloride and dichloroethane; aromatic hydrocarbons such as benzene, toluene and xylene; aliphatic hydrocarbons such as pentane, hexane, cyclohexane and heptane; ethers such as diethyl ether, diisopropyl ether and methyl t-butyl ether; and esters such as butyl acetate, ethyl acetate and methyl acetate. The organic solvent can be used in one or more species.

The amount of the organic solvent, including that of an organic solvent used when the iodine halide or iodine in step b) and/or the metal halide in step c) are added in the form of a solution, is usually from 2 to 200 times the weight of β-carotene, including 5, 10, 20, 30, 40, 50, 60, 70, 80, 100, 120, 140, 150, 160, 170, 180, 190 and all values and subranges there between. Depending on the amount of the organic solvent, a part of β-carotene may remain in the solid form suspended in the reaction mixture. However, such a suspension does not inhibit the progress of the reaction.

The amount of water, including that of water used, when the iodine halide or iodine in step b) and/or the metal halide in step c) are added in the form of a solution, is usually from 1 to 50 times the total weight of the alkali metal chlorate and the alkali metal bromate, including 5, 10, 15, 20, 25, 30, 35, 40, 45 and all values and subranges there between.

Upon the oxidization of β-carotene according to the present invention, the pH of the reaction mixture is preferably from 2 to 8 and more preferably from 3 to 7, including 2.5, 3.5, 4.5, 6, 6.5, 7.5 and all values and subranges there between.

The oxidization of β-carotene according to the present invention is conducted usually at a temperature of 0 to 30° C. and preferably at a temperature of 20 to 30° C., including 5, 10, 15, 23, 25, 27, 29° C. and all values and subranges there between.

The oxidization of β-carotene according to the present invention is preferably conducted in the atmosphere of an inert gas such as nitrogen or argon.

The oxidization of β-carotene according to the present invention is preferably conducted with sufficient stirring.

The progress of oxidization of β-carotene according to the present invention can be detected by such a manner as thin layer chromatography (TLC) or high-performance liquid chromatography (HPLC). In the oxidization according to the present invention, the time until the β-carotene has disappeared is different depending on the reaction conditions. When the iodine halide or iodine in step b) and the metal iodide in step c) are used in the amount that the molar ratio of the metal iodide based on the iodine halide or iodine is 0.5–10, the time is usually about 5–180 minutes.

After the reaction has completed, canthaxanthin, a product, can be separated using standard processes. An example of such a process comprises allowing the reaction mixture to stand still thereby separating into a water phase and an organic phase, collecting the organic phase, washing the organic phase, if necessary, with aqueous sodium thiosulfate, aqueous sodium sulfite, water or the like, and removing the organic solvent from the organic phase.

The resultant canthaxanthin can be further purified by standard methods, such as column chromatography or crystallization.

An example a crystallization process comprises dissolving canthaxanthin in a halogenated hydrocarbon such as methylene chloride or chloroform at an elevated temperature, adding to the resultant solution an organic solvent such as methanol, ethanol or acetone, cooling the resulting solution, and collecting the precipitated crystal.

Prior to the above-mentioned purification, an isomer having a carbon-carbon double bond of a cis-type, present in the product, may be isomerized to a compound having all carbon-carbon double bonds of a trans-type (an all-trans isomer), if necessary. Such isomerization can easily be effected by heating the product. An example of the method for the isomerization is a process comprising adding to the resultant canthaxanthin a diluent such as methyl ethyl ketone, acetone, hexane, heptane, isopropyl ether or water in an amount of 1–10 times the weight of the obtained canthaxanthin, and then heating and refluxing the resulting mixture for 0.5–10 hours.

According to the present invention, canthaxanthin can be produced for a short time, with efficiency and in an industrially advantageous manner.

Other features of the present invention will become apparent in the course of the following descriptions of exemplary embodiments which are given for illustration of the present invention and are not intended to be limiting thereof.

EXAMPLES

Example 1

A three-necked flask having an inner volume of 5 liters was charged with a solution of 75 g (0.14 mole) of β-carotene in 600 ml of methylene chloride and a solution of 223.55 g (2.1 moles) of sodium chlorate in 2 liters of water under the atmosphere of nitrogen. To the resultant mixture, a solution of 2.13 g (8.4 mmol) of iodine and 4.65 g (28 mmol) of potassium iodide in a mixture of 150 ml of methylene chloride and 250 ml of water was added all at once at 17° C. under vigorous agitation. After the addition, temperature of the reaction mixture was raised to 24° C. The resultant mixture was stirred at room temperature for 110 minutes. At this time β-carotene had disappeared and the pH of the reaction mixture was 7. The resulting reaction mixture was allowed to stand still to separate into an upper water phase and a lower organic phase. The organic phase was collected and washed successively with 1 liter of water, 1 liter of 1% aqueous sodium thiosulfate and 1 liter of water. The solvent was removed under reduced pressure to yield 96.18 g of a crude product. Analysis by HPLC showed that this crude product contained 60.04 g of canthaxanthin (yield: 76%, and the content of the all-trans isomer thereof: 52%).

To the resultant crude product 200 ml of water were added, and the resulting mixture was heated and refluxed for 7 hours. After cooling to 35° C., 1 liter of methylene chloride was added to the mixture so as to dissolve the organic compound therein. The methylene chloride phase was separated, and 340 ml of methanol were added thereto. The solution was cooled to 10° C. The precipitated crystal was collected by filtration and dried to yield 19.75 g of crystal of canthaxanthin having a high purity (purity: 99%, and the content of the all-trans isomer: 99%).

On the other hand, the solvent was removed from the filtrate, and the resultant residue was dissolved in methylene chloride at an elevated temperature. Crystallization from the resultant solution with methanol in the same manner as above yielded 24.17 g of canthaxanthin crystal (purity: 96%, and the content of the all-trans isomer: 99%).

Analysis conditions of HPLC in the above were as follows.

Column: ZORBAX SIL length 250 mm×4.6 mm I.D.
Eluent: hexane/ethyl acetate=8/2 (vol/vol)
Detector: UV detector (wavelength: 275 nm)

Example 2

A three-necked flask having an inner volume of 300 ml was charged with a solution of 5 g (9.31 mmol) of β-carotene in 40 ml of methylene chloride and a solution of 29.7 g (0.279 mole) of sodium chlorate in 100 ml of water under the atmosphere of nitrogen. To the resultant mixture, a solution of 0.15 g (0.93 mmol) of iodine chloride and 0.32 g (1.9 mmol) of potassium iodide in a mixture of 10 ml of methylene chloride and 50 ml of water was added all at once at 20° C. under vigorous agitation. After the addition, the temperature of the reaction mixture was raised to 24° C. The resultant mixture was stirred at room temperature for 90 minutes. At this time, β-carotene had disappeared and the pH of the reaction mixture was 7. The resulting reaction mixture was allowed to stand still to separate into an upper water phase and a lower organic phase. The organic phase was collected and washed successively with 100 ml of water, 100 ml of 1% aqueous sodium thiosulfate and 100 ml of water. The solvent was removed under reduced pressure to yield 9.2 g of a crude product. Analysis by HPLC under the same analysis conditions as in Example 1 showed that this crude product contained 3.55 g of canthaxanthin (yield: 67.5%).

Example 3

The same procedures as in Example 2 were repeated except that 0.155 g (0.93 mmol) of iodine bromide was used instead of iodine chloride to yield a crude product containing 3.47 g of canthaxanthin (yield: 65.9%) by the reaction time of 90 minutes. After 90 minutes reaction time, the β-carotene had disappeared and the pH of the reaction mixture was 7.

Example 4

The same procedures as in Example 2 were repeated except that 0.22 g (0.93 mmol) of iodine trichloride was used instead of iodine chloride to yield a crude product containing 2.54 g of canthaxanthin (yield: 48.3%) by the reaction time of 42 minutes. After 42 minutes of reaction time, the β-carotene had disappeared and the pH of the reaction mixture was 2.

Example 5

The same procedures as in Example 2 were repeated except that 0.24 g (0.93 mmol) of iodine was used instead of iodine chloride and 40 ml of chloroform was used instead of methylene chloride to yield a crude product containing 3.73 g of canthaxanthin (yield: 70.9%) by the reaction time of 90 minutes. After 90 minutes reaction time, the β-carotene had disappeared and the pH of the reaction mixture was 7.

Comparative Example 1

The same procedures as in Example 2 were repeated without any use of potassium iodide to yield a crude product containing 0.36 g of canthaxanthin (yield: 6.8%) by the reaction time of 90 minutes. After 90 minutes reaction time, it was observed that β-carotene remained.

Comparative Example 2

The same procedures as in Example 2 were repeated except that 0.24 g (0.93 mmol) of iodine was used instead of iodine chloride and potassium iodide to yield a crude product containing 1.55 g of canthaxanthin (yield: 29.5%) by the reaction time of 90 minutes. After 90 minutes of reaction time, it was observed that β-carotene remained.

Obviously, numerous modifications and variations are possible in light of the above teachings. It is therefore to be understood that within the scope of the appended claims the present invention may be practiced otherwise than as specifically described herein.

The entire disclosures of the specifications, claims and summaries of Japanese Patent Application No. Hei 11-162577 filed on Jun. 9, 1999 is incorporated herein by reference.

What is claimed is:

1. A process for producing canthaxanthin comprising the steps of:
   a) mixing β-carotene with an alkali metal chlorate or an alkali metal bromate in water and an organic solvent immiscible with water;
   b) adding an iodine halide or iodine; and
   c) adding a metal iodide,
      wherein the total amount of added iodine halide and/or iodine in step b) is 1 to 20% per mole of β-carotene, the amount of added metal iodide in step c) is 1–40% per mole of β-carotene and the molar ratio of the added metal iodide to the added iodine halide or iodine is 0.5 to 10.

2. The process of claim 1, wherein the adding steps b) and c) are performed at the same time.

3. The process of claim 1, wherein the molar ratio of the metal iodide in c) to the iodine halide or iodine in b) is from 2 to 5.

4. The process of claim 1, wherein the pH of a reaction mixture after the adding step c) is from 2 to 8.

5. The process of claim 1, wherein the pH of a reaction mixture after the adding step c) is from 3 to 7.

6. The process of claim 1, wherein the amount of metal iodide is from 5 to 30% per mole of β-carotene.

7. The process of claim 1, wherein the metal iodide is selected from the group consisting of lithium iodide, sodium iodide, potassium iodide, magnesium iodide, calcium iodide, silver iodide, copper (I) iodide and copper (II) iodide.

8. The process of claim 1, wherein the alkali metal chlorate or an alkali metal bromate is selected from the group consisting of lithium chlorate, sodium chlorate, potassium chlorate, lithium bromate, sodium bromate and potassium bromate.

9. The process of claim 1, wherein the alkali metal chlorate or an alkali metal bromate is in an amount from 1 to 100 times the weight of β-carotene.

10. The process of claim 1, wherein the organic solvent immiscible in water is selected from the group consisting of halogenated hydrocarbons, aromatic hydrocarbons, aliphatic hydrocarbons, ethers, and esters.

11. The process of claim 1, wherein the water is in an amount from 1 to 50 times the total weight of the alkali metal chlorate and the alkali metal bromate.

12. The process of claim 1, wherein the process is conducted at a temperature of from 0 to 30° C.

13. The process of claim 1, wherein the process is conducted at a temperature of from 20 to 30° C.

14. The process of claim 1 further comprising isolating the canthaxanthin produced by the process.

* * * * *